US012805818B2

(12) United States Patent
Wörlein et al.

(10) Patent No.: US 12,805,818 B2
(45) Date of Patent: Nov. 24, 2026

(54) DETERMINING ELECTRODE ORIENTATION USING OPTIMIZED IMAGING PARAMETERS

(71) Applicant: Brainlab AG, Munich (DE)

(72) Inventors: Swen Wörlein, Munich (DE); Rainer Birkenbach, Erding (DE)

(73) Assignee: Brainlab SE, Munich (DE)

( * ) Notice: Subject to any disclaimer, the term of this patent is extended or adjusted under 35 U.S.C. 154(b) by 0 days.

(21) Appl. No.: 18/865,760

(22) PCT Filed: Jun. 29, 2022

(86) PCT No.: PCT/EP2022/067923
§ 371 (c)(1),
(2) Date: Nov. 14, 2024

(87) PCT Pub. No.: WO2024/002476
PCT Pub. Date: Jan. 4, 2024

(65) Prior Publication Data
US 2025/0114056 A1 Apr. 10, 2025

(51) Int. Cl.
*A61B 6/12* (2006.01)

(52) U.S. Cl.
CPC .................................... *A61B 6/12* (2013.01)

(58) Field of Classification Search
CPC ........................................................ A61B 6/12
See application file for complete search history.

(56) References Cited

U.S. PATENT DOCUMENTS

| | | | | |
|---|---|---|---|---|
| 2007/0274450 | A1* | 11/2007 | Niessen | A61B 6/547 378/197 |
| 2008/0171936 | A1* | 7/2008 | Homan | A61B 6/4441 600/431 |
| 2017/0177827 | A1* | 6/2017 | Achatz | A61N 1/37235 |
| 2020/0237326 | A1* | 7/2020 | Achatz | A61N 1/0534 |
| 2022/0061784 | A1* | 3/2022 | Baxter, III | G06T 7/73 |
| 2022/0175458 | A1* | 6/2022 | Pathak | G16H 50/20 |

* cited by examiner

*Primary Examiner* — Patricia J Park
(74) *Attorney, Agent, or Firm* — Tucker Ellis LLP

(57) ABSTRACT

A computer-implemented method determines the position of a stimulation electrode. The method encompasses determination of the orientation of a medical stimulation electrode from medical image data showing an image of the electrode. A first scan is generated from which the position of the electrode is determined, and a second scan with optimized imaging parameters is generated using the same or a different imaging modality. The second scan shows a more precise image of the electrode and is used to determine the rotational orientation of the electrode along its longitudinal axis.

13 Claims, 10 Drawing Sheets

DETERMINING ELECTRODE ORIENTATION USING OPTIMIZED IMAGING PARAMETERS

RELATED APPLICATION DATA

This application is a National Phase application of International Application No. PCT/EP2022/067923, filed Jun. 29, 2022, the contents of which are incorporated herein by reference.

FIELD

The present invention relates to a computer-implemented method of determining a position of a stimulation electrode, a corresponding computer program, a computer-readable storage medium storing such a program and a computer executing the program, as well as a medical system comprising an electronic data storage device and the aforementioned computer.

BACKGROUND

Currently, for three-dimensional and two-dimensional medical images, the following procedures are known for determining the orientation of a medical stimulation electrode:

The current procedure for three-dimensional images can be outlined as follows: First, a three-dimensional image showing the electrode is created with a medical imaging apparatus (e.g. CT or MR scanner). Then, a computer algorithm is used to identify the electrode and specific characteristics of it in the three-dimensional image such as its tip and its longitudinal axis and, if the electrode is not symmetrical around the longitudinal axis, its orientation. The orientation can be identified by e.g. the asymmetric properties of the three-dimensionally reconstructed electrode like directional contacts and/or a specific marker or by using specific artefacts caused by these asymmetric properties (e.g. in a CT scanner metal artifacts of the contacts and marker). With this information identified by the algorithm, the spatial position of the electrode in the three-dimensional image is determined.

The current procedure for projected two-dimensional images can be outlined as follows:

First, a series of projected two-dimensional images is created with an medical imaging apparatus (e.g. a cone beam CT device) that contains a sufficient number of images showing the electrode from different angles to allow for a three-dimensional spatial localization of the electrode. These two-dimensional images are co-registered to a common coordinate system so that their relative position in three-dimensional space is identified. Then, a computer algorithm is used to identify the electrode and specific characteristics of it in the two-dimensional images such as its tip and its longitudinal axis and, if the electrode is not symmetrical around the longitudinal axis, its orientation. The orientation can be identified by e.g. the asymmetric properties of the electrode like directional contacts and/or a specific marker that show up differently depending of the varying imaging angles used for the two-dimensional images. With this information identified by the algorithm, the spatial position of the electrode in the same three-dimensional coordinate system to which the two-dimensional images are registered can be determined.

However, for the known approaches, the following applies.

If a general purpose scan is used (e.g a CT overview scan of the head) the resolution is limited for efficiency (scanning time, image set size) and/or to minimize the x-ray dose.

This limitation in image resolution does reduce the precision of the electrode localization, especially if the electrode is small.

This precision could be improved with a higher resolution with the drawbacks shown above.

Due to device limitations (at maximum volume*resolution) it might even not be possible to create a scan that shows the electrode in its entire shape (which is needed for determining the complete implant position) and at the same time with a resolution high enough to identify the characteristics for a precise localization of the tip and especially of the orientation of the electrode.

The present invention has the object of providing more precise means for determining the orientation of a medical stimulation electrode from a medical image.

The present invention can be used for . . . procedures e.g. in connection with a system for planning and reviewing electrode positions such as Brainlab Elements Trajectory Planning.

Aspects of the present invention, examples and exemplary steps and their embodiments are disclosed in the following. Different exemplary features of the invention can be combined in accordance with the invention wherever technically expedient and feasible.

EXEMPLARY SHORT DESCRIPTION

In the following, a short description of the specific features of the present invention is given which shall not be understood to limit the invention only to the features or a combination of the features described in this section.

The disclosed method encompasses determination of the orientation of a medical stimulation electrode from medical image data showing an image of the electrode. A first scan is generated from which the position of the electrode is determined, and a second scan with optimized imaging parameters is generated using the same or a different imaging modality. The second scan shows a for example more precise image of the electrode and is used to determine the rotational orientation of the electrode along its longitudinal axis.

GENERAL DESCRIPTION

In this section, a description of the general features of the present invention is given for example by referring to possible embodiments of the invention.

In general, the invention reaches the aforementioned object by providing, in a first aspect, a computer-implemented medical method of determining a position of a stimulation electrode. The method comprises executing, on at least one processor of at least one computer (for example at least one computer being part of a navigation system), the following exemplary steps which are executed by the at least one processor.

In a (for example first) exemplary step, first medical image data is acquired which describes a first digital medical image of an anatomical body part and the stimulation electrode. For example, the first digital medical image is a digital image defined in three dimensions, for example a tomographic image such as a computed x-ray tomography, a magnetic resonance tomography, or ultrasound tomography; or the first digital medical image is a two-dimensional digital image such as a radiography. For example, the stimulation electrode comprises at least two directional contacts which are spaced apart from another, and wherein an image appearance of at least part of each of at least two spaces in between the at least two directional contacts in the second digital medical images is used to determine the rotational orientation described by the electrode orientation data. This can be done as explained in EP 3 376 960 B1, which is incorporated herein by reference in its entirety. Specifically, the method disclosed therein encompasses acquiring rotational image data which describes (for example, at least one of defines or represents) two-dimensional medical images of (i.e. depicting or showing) an anatomical structure (i.e. the anatomical body part) and the stimulation electrode. Specifically, the two-dimensional images (for example each) depict both the anatomical body part and the stimulation electrode. The two-dimensional medical images have been or are being taken with a two-dimensional medical imaging apparatus or method such as imaging with a C-arm (C-arm x-ray, also called C-arm radiography), by rotational angiography or cone beam computed x-ray tomography (cone beam CT). For example, the two-dimensional images have been or are being taken during rotation of the medical imaging apparatus relative to the anatomical body part, i.e. each two-dimensional image has been taken at a different rotational position of the medical imaging apparatus relative to the position of the anatomical body part and the stimulation electrode, for example such that immediately subsequent positions of the medical imaging apparatus are associated with two-dimensional images taken immediately subsequently in the order of their generation. For example, each two-dimensional medical image is associated with a different imaging perspective (for example, relative to the position of the anatomical structure). The rotational image data further describes, for each of the two-dimensional medical images, an imaging perspective relative to the anatomical body part associated with the respective two-dimensional dimensional medical image. The imaging perspective is preferably defined by the position of the medical imaging apparatus which the medical imaging apparatus had relative to the anatomical body part and for example the electrode when the respective two-dimensional image was generated.

For example, determining the electrode orientation data includes determining, based on the first medical image data, an image appearance of the orientation marker, for example by at least one of:

- segmenting an image appearance of the electrode in each of the first digital medical images;
- edge detection of constituents of the first digital medical images;
- comparing the image appearance of the electrode in the second digital medical images to previously acquired and predetermined electrode template data describing constructional data of the stimulation electrode.

For a cone beam CT scanner the orientation of the stimulation electrode is for example determined by first creating a limited number of overview two-dimensional images of the electrode projected from different angles (e.g. every 30 degrees). On these images, the electrode is localized by an algorithm and the characteristics of the electrode are analyzed. With this analysis it is determined which angles would be beneficial to perform a more precise localization of the electrode. An example of such a characteristic is the shape of a rotational asymmetric marker. This looks different from different angles, e.g. flatter from some angles and bolder from others. If, for example, the orientation were now determined by finding the angle that is orthogonal to the flat side of the marker, the interesting angles for the next series of two-dimensional images could be around the angle of the current two-dimensional image with the flattest shape visible. With this information, a second series of two-dimensional images can be created, also with optimized parameters to achieve a precise electrode localization (dose, FOV, focus, collimator settings).

In a (for example second) exemplary step, electrode position data is determined based on the first medical image data, wherein the electrode position data describes a position of the stimulation electrode relative to the anatomical body part. For example, the position is determined by analysing (e.g. segmenting) the first digital medical image for the position of an imaging artefact caused by and/or associated with the stimulation electrode. For example, the electrode position data is determined by determining the position of an artefact in the first medical image representing the imaging response of the stimulation electrode to imaging radiation used to generate the first medical image data.

In a (for example third) exemplary step, second digital medical image data is acquired based on the electrode position data, wherein the second digital medical image data describes a set of second digital medical images of the stimulation electrode which were taken for example from different imaging directions relative to the stimulation electrode. For example, the second digital medical images are digital images defined in three dimensions, for example tomographic images such as computed x-ray tomographies, magnetic resonance tomographies, or ultrasound tomographies; or the second digital medical images are two-dimensional digital images such as a radiographies. The imaging geometry used for generating the second digital medical image data is determined based on the electrode position data such that an image rendering of the electrode in the second digital medical images is generated. For example, at least one of the imaging directions at which the second digital medical images were generated is determined based on the first medical image data. For example, the at least one imaging direction is perpendicular to the longitudinal axis of the stimulation electrode.

In a (for example fourth) exemplary step, electrode orientation data is determined based on the second digital medical image data, wherein the electrode orientation data describes a rotational orientation of the electrode around its longitudinal axis. For example, the orientation of the electrode is determined based on the second digital medical image data, which may lead to a more precise determination of the orientation than determining it on the basis of the first medical image data.

In an example of the method according to the first aspect, at least one of the first medical image data or the second digital medical image data is three-dimensional image data, for example tomographic image data. In an example of the method according to the first aspect, at least one of the first medical image data or the second digital medical image data is two-dimensional image data, for example radiographic image data.

In an example of the method according to the first aspect, an imaging parameter of a medical imaging apparatus is optimized based on at least one of the first medical image data or the second digital medical image data, for example for generating third medical image data which describes a third medical image of the stimulation electrode. For example, the imaging parameter is at least one of imaging radiation dose, field of view, focus or collimator setting of a medical imaging apparatus used to generate at least one of the first medical image data, second medical image data and third medical image data. For example, the third medical image data is two- or three-dimensional image data, for example a radiography or a tomography.

In a second aspect, the embodiments of the claimed invention are directed to a computer program product comprising instructions which, when the program is executed by at least one computer, causes the at least one computer to carry out method according to the third aspect. A computer program stored on a disc is a data file, and when the file is read out and transmitted it becomes a data stream for example in the form of a (physical, for example electrical, for example technically generated) signal. For example, the signal, for example the signal wave is constituted to be transmitted via a computer network, for example LAN, WLAN, WAN, mobile network, for example the internet. For example, the signal, is constituted to be transmitted by optic or acoustic data transmission. The embodiments of the claimed invention according to the fourth aspect therefore may alternatively or additionally relate to a computer program product storing data representative of the aforementioned program, i.e. comprising the program.

In a third aspect, the invention is directed to a computer-readable storage medium on which the program according to the second aspect is stored. The program storage medium is for example non-transitory.

In a fourth aspect, the invention is directed to at least one computer (for example, a computer), comprising at least one processor (for example, a processor), wherein the program according to the second aspect is executed by the processor, or wherein the at least one computer comprises the computer-readable storage medium according to the third aspect.

In a fifth aspect, the invention is directed to a medical system, comprising:

a) the at least one computer according to the fourth aspect, wherein the processor is configured to determine, by the at least one processor and for example based on the rotational image data, an image appearance of the orientation marker by comparing the image appearance of the electrode in the second digital medical images to previously acquired and predetermined electrode template data describing constructional data of the stimulation electrode;

b) an electronic data storage device storing at least the electrode template data; and c) a first medical imaging apparatus configured to generate the first medical image data, d) a second medical imaging apparatus configured to generate the second digital medical image data, wherein the at least one computer is operably coupled to the first medical imaging apparatus for acquiring, from the first medical imaging apparatus, the first medical image data;

the second medical imaging apparatus for acquiring, from the second medical imaging apparatus, the second digital medical image data; and the at least one electronic data storage device for acquiring, from the data storage device, at least the electrode template data.

In an example of the system according to the fifth aspect, the first medical imaging apparatus and the second medical imaging apparatus are identical, i.e. the system comprises only one medical imaging apparatus.

For example, the invention does not involve or in particular comprise or encompass an invasive step which would represent a substantial physical interference with the body requiring professional medical expertise to be carried out and entailing a substantial health risk even when carried out with the required professional care and expertise.

For example, the invention does not comprise a step of implanting the stimulation electrode for example into an anatomical body part. More particularly, the invention does not involve or in particular comprise or encompass any surgical or therapeutic activity. The invention is instead directed as applicable to imaging the stimulation electrode and analyzing the resulting image data For this reason alone, no surgical or therapeutic activity and in particular no surgical or therapeutic step is necessitated or implied by carrying out the invention.

Definitions

In this section, definitions for specific terminology used in this disclosure are offered which also form part of the present disclosure.

The method in accordance with the invention is for example a computer-implemented method. For example, all the steps or merely some of the steps (i.e. less than the total number of steps) of the method in accordance with the invention can be executed by a computer (for example, at least one computer). An embodiment of the computer implemented method is a use of the computer for performing a data processing method. An embodiment of the computer implemented method is a method concerning the operation of the computer such that the computer is operated to perform one, more or all steps of the method.

The computer for example comprises at least one processor and for example at least one memory in order to (technically) process the data, for example electronically and/or optically. The processor being for example made of a substance or composition which is a semiconductor, for example at least partly n- and/or p-doped semiconductor, for example at least one of II-, III-, IV-, V-, VI-semiconductor material, for example (doped) silicon and/or gallium arsenide. The calculating or determining steps described are for example performed by a computer. Determining steps or calculating steps are for example steps of determining data within the framework of the technical method, for example within the framework of a program. A computer is for example any kind of data processing device, for example electronic data processing device. A computer can be a device which is generally thought of as such, for example desktop PCs, notebooks, netbooks, etc., but can also be any programmable apparatus, such as for example a mobile phone or an embedded processor. A computer can for example comprise a system (network) of "sub-computers", wherein each sub-computer represents a computer in its own right. The term "computer" includes a cloud computer, for example a cloud server. The term computer includes a server resource. The term "cloud computer" includes a cloud computer system which for example comprises a system of at least one cloud computer and for example a plurality of operatively interconnected cloud computers such as a server farm. Such a cloud computer is preferably connected to a wide area network such as the world wide web (WWW) and located in a so-called cloud of computers which are all connected to the world wide web. Such an infrastructure is used for "cloud computing", which describes computation, software, data access and storage services which do not require the end user to know the physical location and/or configuration of the computer delivering a specific service. For example, the term "cloud" is used in this respect as a metaphor for the Internet (world wide web). For example, the cloud provides computing infrastructure as a service (IaaS). The cloud computer can function as a virtual host for an operating system and/or data processing application which is used to execute the method of the invention. The cloud computer is for example an elastic compute cloud (EC2) as provided by Amazon Web Services™. A computer for example comprises interfaces in order to receive or output data and/or perform an analogue-to-digital conversion. The data are for example data which represent physical properties and/or which are generated from technical signals. The technical signals are for example generated by means of (technical) detection devices (such as for example devices for detecting marker devices) and/or (technical) analytical devices (such as for example devices for performing (medical) imaging methods), wherein the technical signals are for example electrical or optical signals. The technical signals for example represent the data received or outputted by the computer. The computer is preferably operatively coupled to a display device which allows information outputted by the computer to be displayed, for example to a user. One example of a display device is a virtual reality device or an augmented reality device (also referred to as virtual reality glasses or augmented reality glasses) which can be used as "goggles" for navigating. A specific example of such augmented reality glasses is Google Glass (a trademark of Google, Inc.). An augmented reality device or a virtual reality device can be used both to input information into the computer by user interaction and to display information outputted by the computer. Another example of a display device would be a standard computer monitor comprising for example a liquid crystal display operatively coupled to the computer for receiving display control data from the computer for generating signals used to display image information content on the display device. A specific embodiment of such a computer monitor is a digital lightbox. An example of such a digital lightbox is Buzz®, a product of Brainlab AG. The monitor may also be the monitor of a portable, for example handheld, device such as a smart phone or personal digital assistant or digital media player.

The example embodiment also relates to a computer program stored on a non-transient storage medium and comprising instructions that, when executed by a processor device of a computer, cause the computer to carry out the method or methods, for example, the steps of the method or methods, described herein and/or to a computer-readable storage medium (for example, a non-transitory computer-readable storage medium) on which the program is stored and/or to a computer comprising said program storage medium, which for example comprises code means which are adapted to perform any or all of the method steps described herein. The example embodiment also relates to a computer comprising at least one processor and/or the aforementioned computer-readable storage medium and for example a memory, wherein the program is executed by the processor.

Within the framework of the invention, computer program elements can be embodied by hardware and/or software (this includes firmware, resident software, micro-code, etc.). Within the framework of the invention, computer program elements can take the form of a computer program product which can be embodied by a computer-usable, for example computer-readable data storage medium comprising computer-usable, for example computer-readable program instructions, "code" or a "computer program" embodied in said data storage medium for use on or in connection with the instruction-executing system. Such a system can be a computer; a computer can be a data processing device comprising means for executing the computer program elements and/or the program in accordance with the invention, for example a data processing device comprising a digital processor (central processing unit or CPU) which executes the computer program elements, and optionally a volatile memory (for example a random access memory or RAM) for storing data used for and/or produced by executing the computer program elements. Within the framework of the present invention, a computer-usable, for example computer-readable data storage medium can be any data storage medium which can include, store, communicate, propagate or transport the program for use on or in connection with the instruction-executing system, apparatus or device. The computer-usable, for example computer-readable data storage medium can for example be, but is not limited to, an electronic, magnetic, optical, electromagnetic, infrared or semiconductor system, apparatus or device or a medium of propagation such as for example the Internet. The computer-usable or computer-readable data storage medium could even for example be paper or another suitable medium onto which the program is printed, since the program could be electronically captured, for example by optically scanning the paper or other suitable medium, and then compiled, interpreted or otherwise processed in a suitable manner. The data storage medium is preferably a non-volatile data storage medium. The computer program product and any software and/or hardware described here form the various means for performing the functions of the invention in the example embodiments. The computer and/or data processing device can for example include a guidance information device which includes means for outputting guidance information. The guidance information can be outputted, for example to a user, visually by a visual indicating means (for example, a monitor and/or a lamp) and/or acoustically by an acoustic indicating means (for example, a loudspeaker and/or a digital speech output device) and/or tactilely by a tactile indicating means (for example, a vibrating element or a vibration element incorporated into an instrument). For the purpose of this document, a computer is a technical computer which for example comprises technical, for example tangible components, for example mechanical and/or electronic components. Any device mentioned as such in this document is a technical and for example tangible device.

The expression "acquiring data" for example encompasses (within the framework of a computer implemented method) the scenario in which the data are determined by the computer implemented method or program. Determining data for example encompasses measuring physical quantities and transforming the measured values into data, for example digital data, and/or computing (and e.g. outputting) the data by means of a computer and for example within the framework of the method in accordance with the invention. A step of "determining" as described herein for example comprises or consists of issuing a command to perform the determination described herein. For example, the step comprises or consists of issuing a command to cause a computer, for example a remote computer, for example a remote server, for example in the cloud, to perform the determination. Alternatively or additionally, a step of "determination" as described herein for example comprises or consists of receiving the data resulting from the determination described herein, for example receiving the resulting data from the remote computer, for example from that remote computer which has been caused to perform the determination. The meaning of "acquiring data" also for example encompasses the scenario in which the data are received or retrieved by (e.g. input to) the computer implemented method or program, for example from another program, a previous method step or a data storage medium, for example for further processing by the computer implemented method or program. Generation of the data to be acquired may but need not be part of the method in accordance with the invention. The expression "acquiring data" can therefore also for example mean waiting to receive data and/or receiving the data. The received data can for example be inputted via an interface. The expression "acquiring data" can also mean that the computer implemented method or program performs steps in order to (actively) receive or retrieve the data from a data source, for instance a data storage medium (such as for example a ROM, RAM, database, hard drive, etc.), or via the interface (for instance, from another computer or a network). The data acquired by the disclosed method or device, respectively, may be acquired from a database located in a data storage device which is operably to a computer for data transfer between the database and the computer, for example from the database to the computer. The computer acquires the data for use as an input for steps of determining data. The determined data can be output again to the same or another database to be stored for later use. The database or database used for implementing the disclosed method can be located on network data storage device or a network server (for example, a cloud data storage device or a cloud server) or a local data storage device (such as a mass storage device operably connected to at least one computer executing the disclosed method). The data can be made "ready for use" by performing an additional step before the acquiring step. In accordance with this additional step, the data are generated in order to be acquired. The data are for example detected or captured (for example by an analytical device). Alternatively or additionally, the data are inputted in accordance with the additional step, for instance via interfaces. The data generated can for example be inputted (for instance into the computer). In accordance with the additional step (which precedes the acquiring step), the data can also be provided by performing the additional step of storing the data in a data storage medium (such as for example a ROM, RAM, CD and/or hard drive), such that they are ready for use within the framework of the method or program in accordance with the invention. The step of "acquiring data" can therefore also involve commanding a device to obtain and/or provide the data to be acquired. In particular, the acquiring step does not involve an invasive step which would represent a substantial physical interference with the body, requiring professional medical expertise to be carried out and entailing a substantial health risk even when carried out with the required professional care and expertise. In particular, the step of acquiring data, for example determining data, does not involve a surgical step and in particular does not involve a step of treating a human or animal body using surgery or therapy. In order to distinguish the different data used by the present method, the data are denoted (i.e. referred to) as "XY data" and the like and are defined in terms of the information which they describe, which is then preferably referred to as "XY information" and the like.

In the field of medicine, imaging methods (also called imaging modalities and/or medical imaging modalities) are used to generate image data (for example, two-dimensional or three-dimensional image data) of anatomical structures (such as soft tissues, bones, organs, etc.) of the human body. The term "medical imaging methods" is understood to mean (advantageously apparatus-based) imaging methods (for example so-called medical imaging modalities and/or radiological imaging methods) such as for instance computed tomography (CT) and cone beam computed tomography (CBCT, such as volumetric CBCT), x-ray tomography, magnetic resonance tomography (MRT or MRI), conventional x-ray, sonography and/or ultrasound examinations, and positron emission tomography. For example, the medical imaging methods are performed by the analytical devices. Examples for medical imaging modalities applied by medical imaging methods are: X-ray radiography, magnetic resonance imaging, medical ultrasonography or ultrasound, endoscopy, elastography, tactile imaging, thermography, medical photography and nuclear medicine functional imaging techniques as positron emission tomography (PET) and Single-photon emission computed tomography (SPECT), as mentioned by Wikipedia. The image data thus generated is also termed "medical imaging data". Analytical devices for example are used to generate the image data in apparatus-based imaging methods. The imaging methods are for example used for medical diagnostics, to analyse the anatomical body in order to generate images which are described by the image data. The imaging methods are also for example used to detect pathological changes in the human body. However, some of the changes in the anatomical structure, such as the pathological changes in the structures (tissue), may not be detectable and for example may not be visible in the images generated by the imaging methods. A tumour represents an example of a change in an anatomical structure. If the tumour grows, it may then be said to represent an expanded anatomical structure. This expanded anatomical structure may not be detectable; for example, only a part of the expanded anatomical structure may be detectable. Primary/high-grade brain tumours are for example usually visible on MRI scans when contrast agents are used to infiltrate the tumour. MRI scans represent an example of an imaging method. In the case of MRI scans of such brain tumours, the signal enhancement in the MRI images (due to the contrast agents infiltrating the tumour) is considered to represent the solid tumour mass. Thus, the tumour is detectable and for example discernible in the image generated by the imaging method. In addition to these tumours, referred to as "enhancing" tumours, it is thought that approximately 10% of brain tumours are not discernible on a scan and are for example not visible to a user looking at the images generated by the imaging method.

Image fusion can be elastic image fusion or rigid image fusion. In the case of rigid image fusion, the relative position between the pixels of a 2D image and/or voxels of a 3D image is fixed, while in the case of elastic image fusion, the relative positions are allowed to change.

In this application, the term "image morphing" is also used as an alternative to the term "elastic image fusion", but with the same meaning.

Elastic fusion transformations (for example, elastic image fusion transformations) are for example designed to enable a seamless transition from one dataset (for example a first dataset such as for example a first image) to another dataset (for example a second dataset such as for example a second image). The transformation is for example designed such that one of the first and second datasets (images) is deformed, for example in such a way that corresponding structures (for example, corresponding image elements) are arranged at the same position as in the other of the first and second images. The deformed (transformed) image which is transformed from one of the first and second images is for example as similar as possible to the other of the first and second images. Preferably, (numerical) optimisation algorithms are applied in order to find the transformation which results in an optimum degree of similarity. The degree of similarity is preferably measured by way of a measure of similarity (also referred to in the following as a "similarity measure"). The parameters of the optimisation algorithm are for example vectors of a deformation field. These vectors are determined by the optimisation algorithm in such a way as to result in an optimum degree of similarity. Thus, the optimum degree of similarity represents a condition, for example a constraint, for the optimisation algorithm. The bases of the vectors lie for example at voxel positions of one of the first and second images which is to be transformed, and the tips of the vectors lie at the corresponding voxel positions in the transformed image. A plurality of these vectors is preferably provided, for instance more than twenty or a hundred or a thousand or ten thousand, etc. Preferably, there are (other) constraints on the transformation (deformation), for example in order to avoid pathological deformations (for instance, all the voxels being shifted to the same position by the transformation). These constraints include for example the constraint that the transformation is regular, which for example means that a Jacobian determinant calculated from a matrix of the deformation field (for example, the vector field) is larger than zero, and also the constraint that the transformed (deformed) image is not self-intersecting and for example that the transformed (deformed) image does not comprise faults and/or ruptures. The constraints include for example the constraint that if a regular grid is transformed simultaneously with the image and in a corresponding manner, the grid is not allowed to interfold at any of its locations. The optimising problem is for example solved iteratively, for example by means of an optimisation algorithm which is for example a first-order optimisation algorithm, such as a gradient descent algorithm. Other examples of optimisation algorithms include optimisation algorithms which do not use derivations, such as the downhill simplex algorithm, or algorithms which use higher-order derivatives such as Newton-like algorithms. The optimisation algorithm preferably performs a local optimisation. If there is a plurality of local optima, global algorithms such as simulated annealing or generic algorithms can be used. In the case of linear optimisation problems, the simplex method can for instance be used.

In the steps of the optimisation algorithms, the voxels are for example shifted by a magnitude in a direction such that the degree of similarity is increased. This magnitude is preferably less than a predefined limit, for instance less than one tenth or one hundredth or one thousandth of the diameter of the image, and for example about equal to or less than the distance between neighbouring voxels. Large deformations can be implemented, for example due to a high number of (iteration) steps.

The determined elastic fusion transformation can for example be used to determine a degree of similarity (or similarity measure, see above) between the first and second datasets (first and second images). To this end, the deviation between the elastic fusion transformation and an identity transformation is determined. The degree of deviation can for instance be calculated by determining the difference between the determinant of the elastic fusion transformation and the identity transformation. The higher the deviation, the lower the similarity, hence the degree of deviation can be used to determine a measure of similarity.

A measure of similarity can for example be determined on the basis of a determined correlation between the first and second datasets.

BRIEF DESCRIPTION OF THE DRAWINGS

In the following, the invention is described with reference to the appended figures which give background explanations and represent specific embodiments of the invention.

The scope of the invention is however not limited to the specific features disclosed in the context of the figures, wherein.

DESCRIPTION OF EMBODIMENTS

Figure 1:
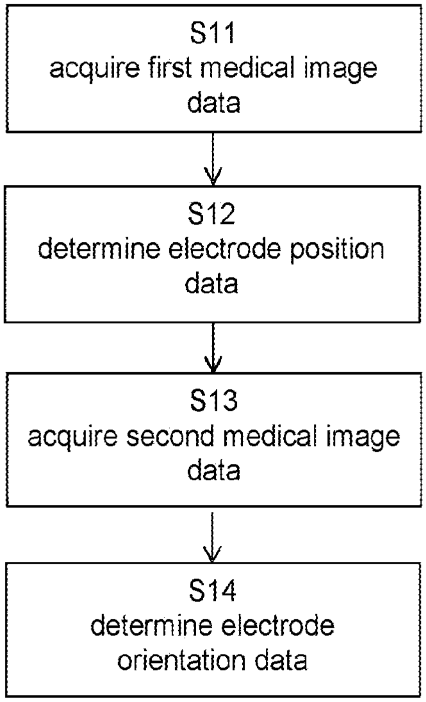
FIG. 1 illustrates the basic steps of the method according to the first aspect.

FIG. 1 illustrates the basic steps of the method according to the first aspect, in which step S11 encompasses acquisition of the first medical image data, step S12 encompasses determination of the electrode position data and subsequent step S13 encompasses acquisition of the second medical image data. In step S14, the electrode orientation data is determined.

Figure 2:
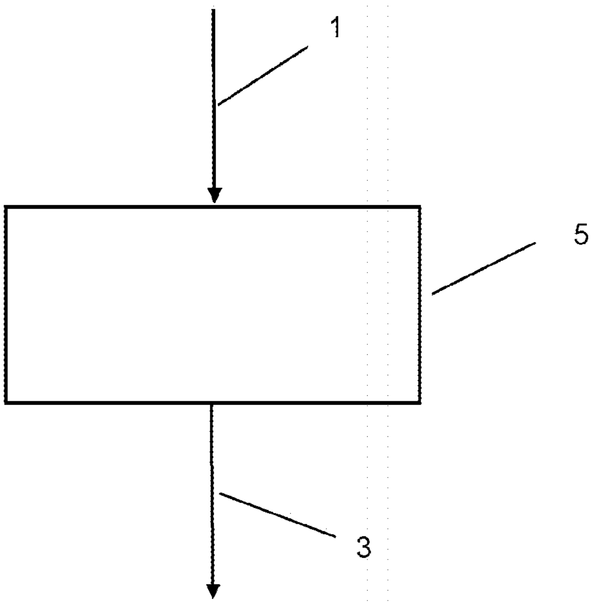
FIG. 2 shows an embodiment of the present invention, specifically the method according to the first aspect.

FIG. 2 illustrates an embodiment of the present invention that includes all essential features of the invention. In this embodiment, the entire data processing which is part of the method according to the first aspect is performed by a computer 5. Reference sign 1 denotes the input of data acquired by the method according to the first aspect into the computer 5 and reference sign 3 denotes the output of data determined by the method according to the first aspect.

To overcome the drawbacks of the existing solutions the electrode localization process is done in an incremental way, allowing for high precision of the localization while keeping the X-Ray dose of the imaging close to the existing solutions or even lower.

Figure 3:
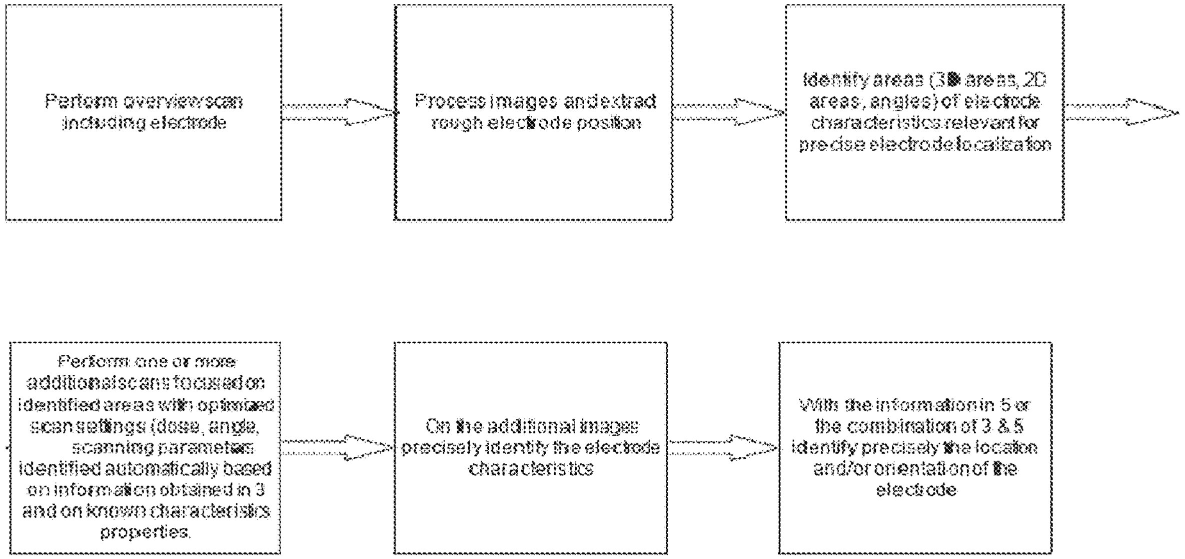
FIG. 3 shows an embodiment of the present invention, specifically the method according to the first aspect.

For computed x-ray tomography (CT) or magnetic resonance (MR) scanners this is achieved by first creating a standard (low resolution, other standard parameters) scan creating an overview three-dimensional image set showing the electrode (or a lower does scan as this is sufficient in this step of the implant localization). Based on this three-dimensional image set the position of the electrode is localized by an algorithm either just roughly or as precise as possible with the available image quality. With the obtained position data of the implant in the scanner coordinate system, a second scan is initiated which is restricted to the area that is required to image the part if the electrode that is required for a high precision spatial localization. For a CT scan this could e.g. be just some image slices at the tip position of the implant and some slices at the marker (or asymmetric contacts). These slices can be images with an optimized set of scanning parameters to localize the implant such as higher dose, smaller slice distance, no metal artifact reduction, optimized beam hardening, axial instead of spiral, gantry tilt, couch position, collimator settings. This second **3*d* image set can then be co-registered to the first image set (e.g. by a co-registering algorithm like mutual information—by utilizing the scanner information of the images to inform a co-registering algorithm—if the patient did not move between the two scans they are already in the same and correct coordinate system—by using a localizer that is included in the scan images or use tracking on the scanner components). On the second image set the detailed information of the implant like tip, marker shape or contact artifacts can now be used to identify the spatial localization of the tip position and the orientation of the implant very precisely. This is shown in the flow diagram of FIG. 3**.

For a cone beam CT scanner this is achieved by first creating a limited number of overview two-dimensional images of the electrode projected from different angles (e.g. every 30 degrees). On these images, the electrode is localized by an algorithm and the characteristics of the electrode are analyzed. With this analysis it is determined which angles would be beneficial to perform a more precise localization of the electrode. An example of such a characteristic is the shape of a rotational asymmetric marker. This looks different from different angles, e.g. flatter from some angles and bolder from others. If, for example, the orientation were now determined by finding the angle that is orthogonal to the flat side of the marker, the interesting angles for the next series of two-dimensional images could be around the angle of the current two-dimensional image with the flattest shape visible. With this information, a second series of two-dimensional images can be created, also with optimized parameters to achieve a precise electrode localization (dose, FOV, focus, collimator settings).

Figure 4:
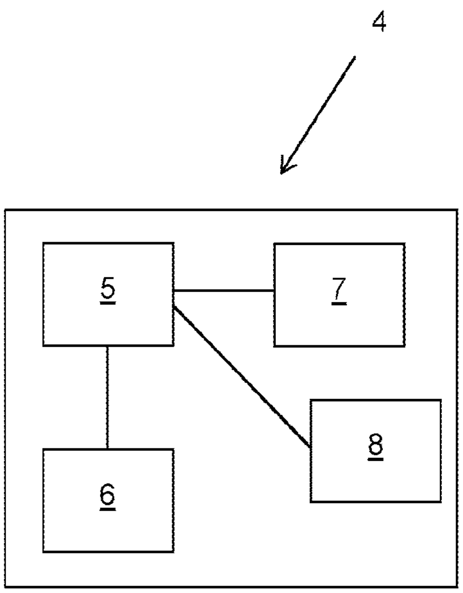
FIG. 4 is a schematic illustration of the system according to the fifth aspect.

FIG. 4 is a schematic illustration of the medical system 4 according to the fifth aspect. The system is in its entirety identified by reference sign 4 and comprises a computer 5, an electronic data storage device (such as a hard disc) 6 for storing at least the first medical image data and the second medical image data. The computer 5 is operably coupled i.a. to a first medical imaging apparatus 7 and a second medical imaging apparatus 8. The components of the medical system 4 have the functionalities and properties explained above with regard to the fifth aspect of this disclosure.

FIGS. 5 to 10 show a special embodiment of detection of a directional deep brain stimulation (DBS) electrode with Loop-X, a mobile computed x-ray tomography scanner provided by Brainlab AG. The problem to be solved can be outlined as follows: directional DBS electrodes have a huge advantage over conventional electrodes but are much more difficult to be programmed by the neurologist. To simplify programming, it is desired to exactly know where (in relation to the patient's anatomy) the electrode is positioned; meaning position (for example of its tip) and the orientation (=rotation) of the electrode. After implantation, it takes a few days until the electrode has found a stable position in the patient's brain.

Figure 5:
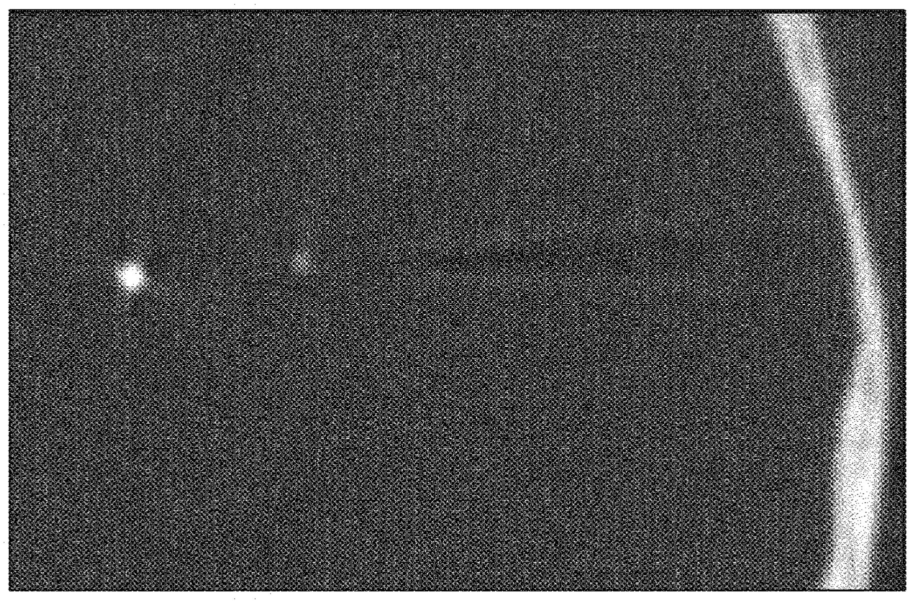
FIGS. 5 to 10 show a special embodiment of detection of a directional stimulation electrode with Loop-x.
Figure 6:
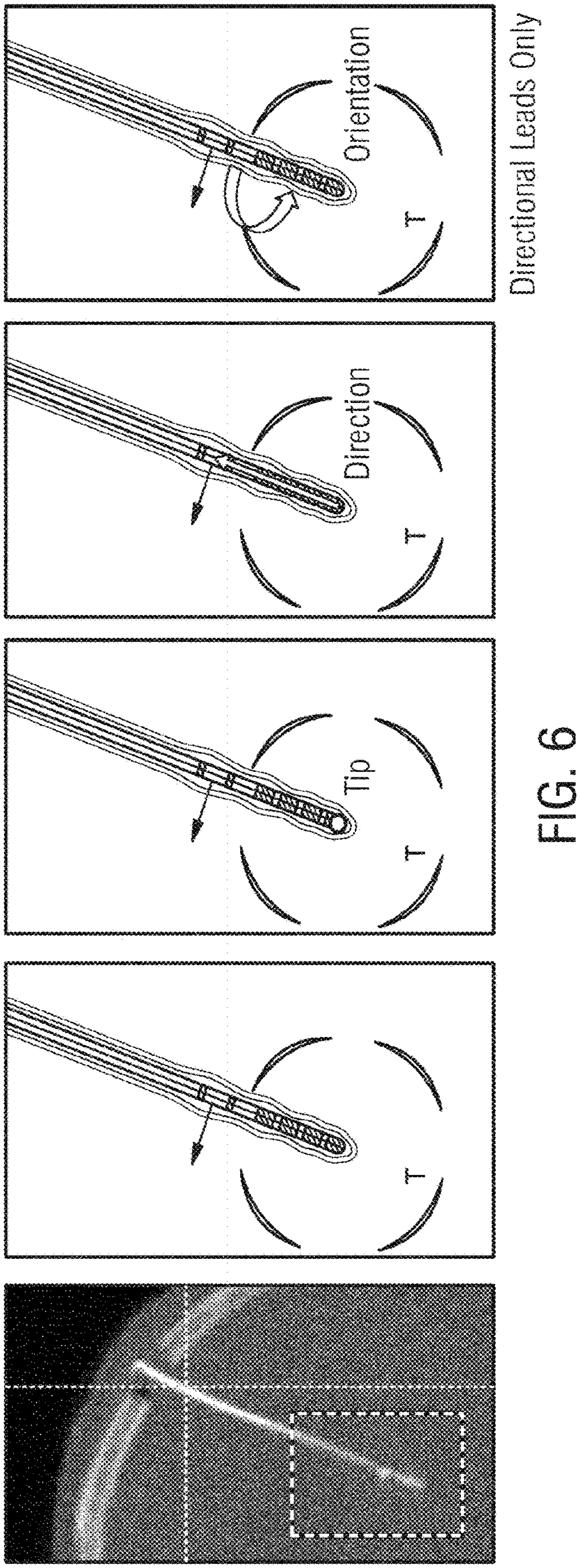

The current approach for determining the electrode orientation is as follows: A few days after implantation, a three-dimensional CT scan is taken. Software for localizing the electrode in the resulting image accurately detects the position of the electrode and estimates the direction of a (directional) electrode. The localization is performed based on the artefacts caused by the electrode in the scan (basically, a CT scanner weakness is used for this). A depiction of such an artefact is given in FIG. 5, and FIG. 6 shows the definition of the tip position and the direction and the orientation of the electrode.

Figure 7:
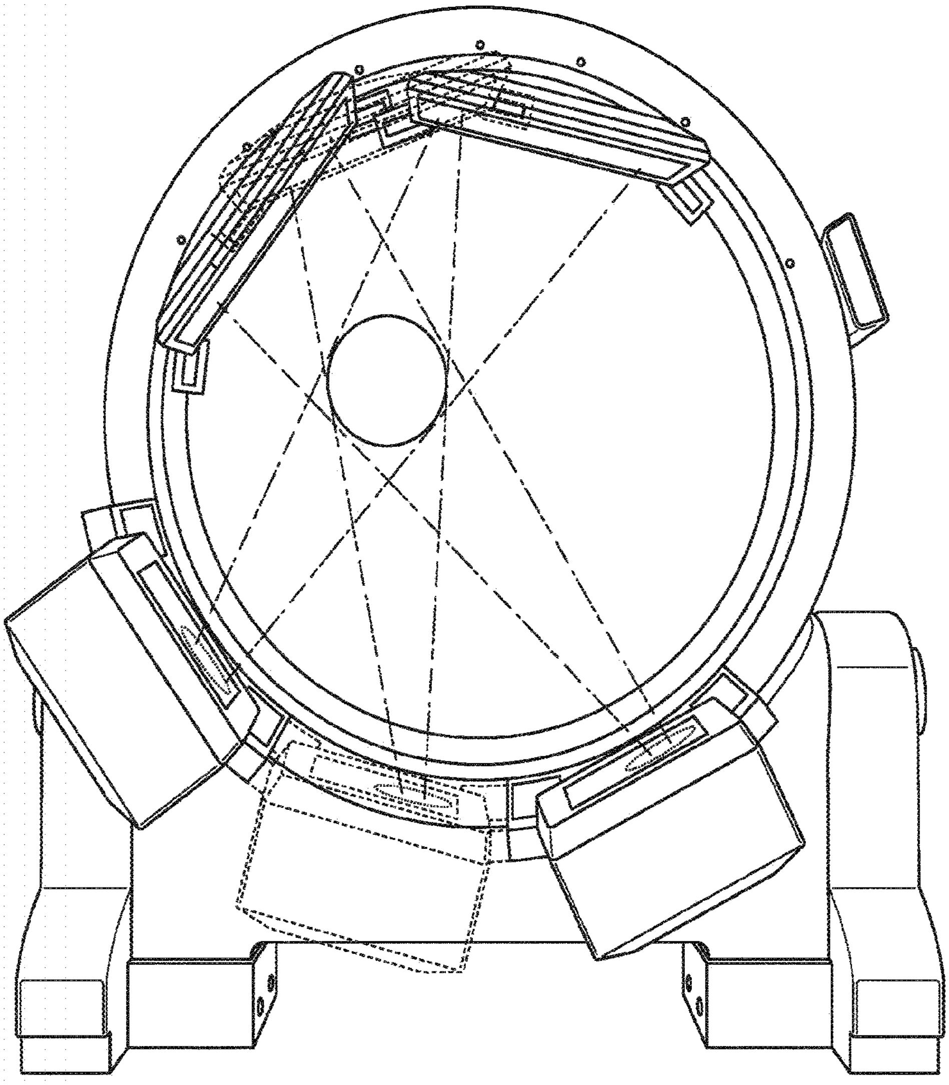
Figure 8:
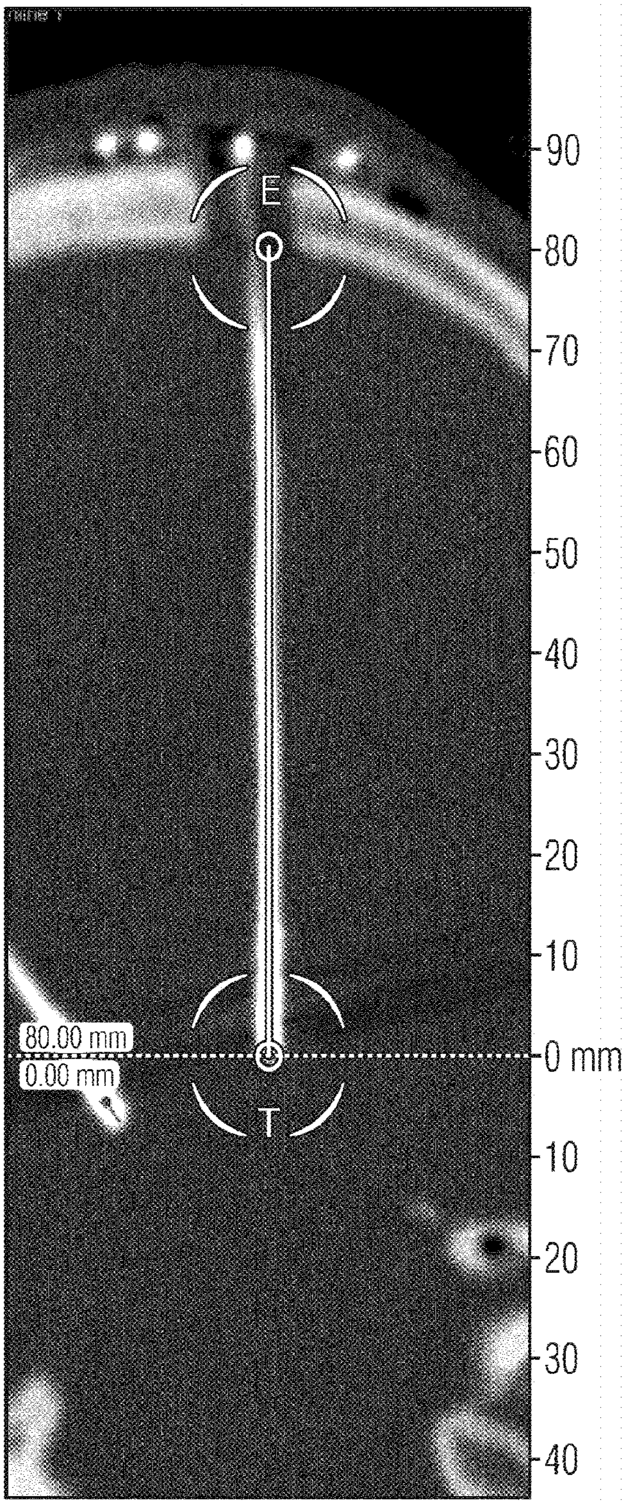

A proposed solution using Loop-X encompasses the following features: Loop-X is used for generating a post-op electrode detection scan. Loop-X can take three-dimensional CT images (cone beam CT) and two-dimensional X-Ray. Loop-X can be robotically controlled to e.g. select a direction in the three-dimensional scan and get a two-dimensional x-ray done in that direction. FIG. 7 shows an illustration of rotational imaging using Loop-X.

Figure 9:
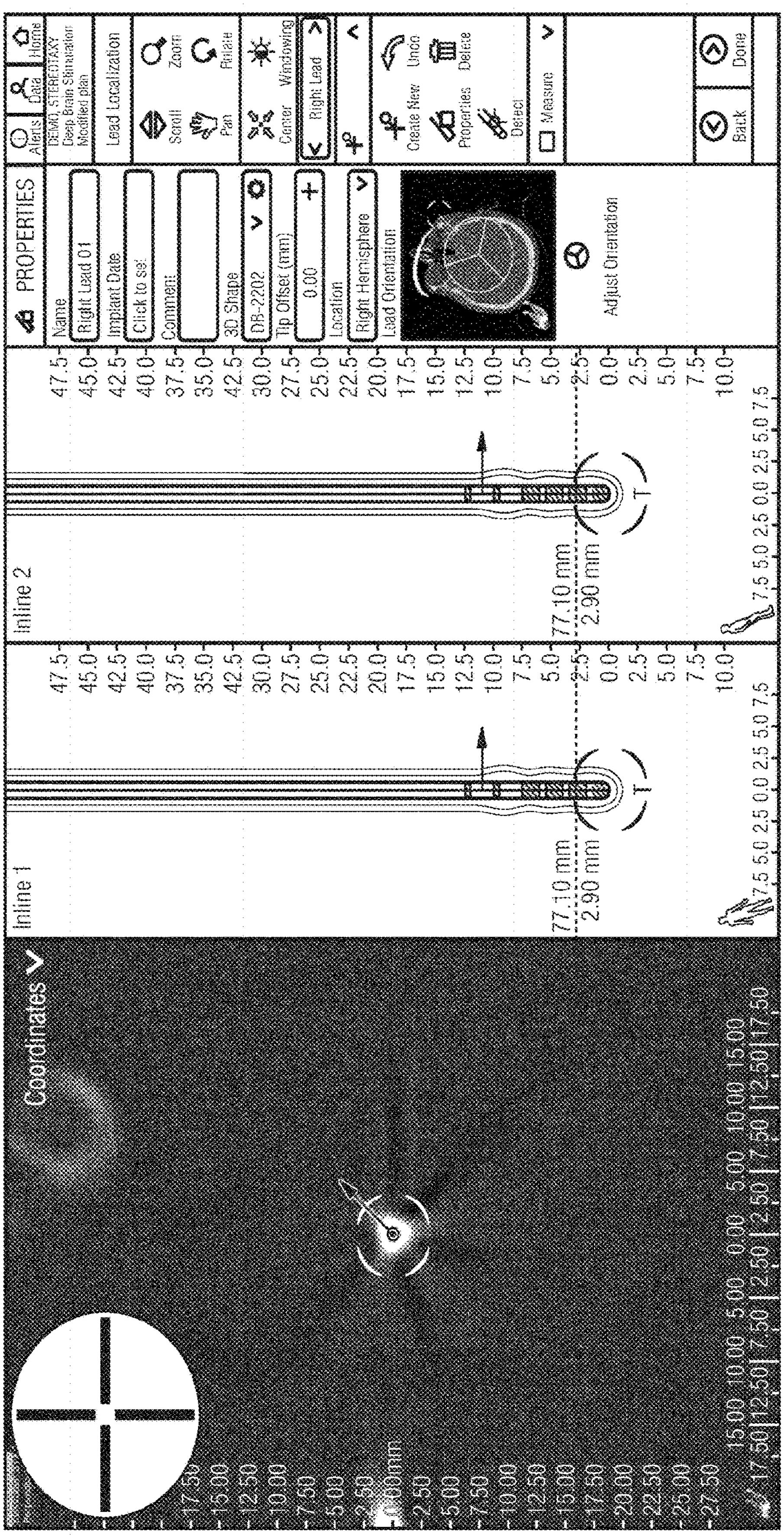
Figure 10:
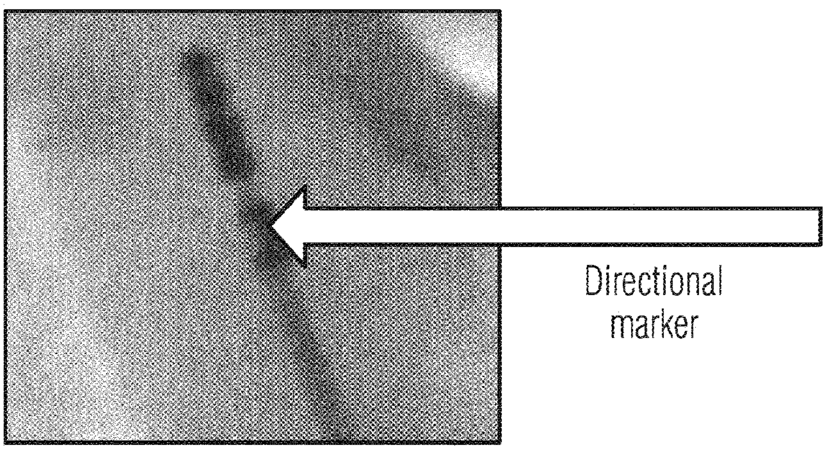

A workflow for automatic detection of position and rotation of a directional DBS electrode includes the following steps:

1. Taking a three-dimensional scan of patients head (Loop-X knows where scan was taken in its own coordinate system)
2. Detecting the position of the electrode in the three-dimensional scan by applying the conventional approach (shown in FIG. 8)
3. Estimating the direction of the electrode by applying the conventional approach based on artifacts or the new approach using special Loop-X presets, as shown in FIG. 9
4. Automatically taking a series of X-Ray images in the perfect direction.
   - Within that range, taking multiple X-ray images around the electrode
   - Optimizing distribution and number of shots based on the detection result
   - Minimizing imaging radiation dose applied to the patient
5. Identifying the direction of the electrode on the two-dimensional scan, including:
   - Detecting the directional marker (as shown in FIG. 10) or unique directional geometry
   - Using classic image processing or machine learning
   - Loop-X knows the imaging directing of the "best x-ray"
   - Calculating the direction of the electrode in the three-dimensional scan and save the result A technical advantage associated with the new approach is accurate detection instead of just estimation of the electrode direction: the new approach has the potential of increasing the accuracy of electrode direction determination.

The invention claimed is:

1. A computer-implemented medical method of determining a position of a stimulation electrode having asymmetric properties provided to the stimulation electrode by directional contacts of the stimulation electrode and/or by an asymmetric marker coupled with the stimulation electrode, the method comprising:

acquiring first medical image data that describes a first digital medical image of an anatomical body part and the stimulation electrode;

determining electrode position data based on the first medical image data, wherein the electrode position data describes a position of an artifact in the first medical image data representing an imaging response of the stimulation electrode having the asymmetric properties to imaging radiation used to generate the first medical image data, wherein the electrode position data describes a position of the stimulation electrode relative to the anatomical body part;

acquiring second digital medical image data based on the position of the artifact described in the electrode position data, wherein the second digital medical image data describes a set of second digital medical images of the stimulation electrode; and determining electrode orientation data based on the second digital medical image data, wherein the electrode orientation data describes a rotational orientation of the stimulation electrode around a longitudinal axis of the stimulation electrode.

2. The method according to claim 1, wherein at least one of the first medical image data and/or the second digital medical image data comprises tomographic three-dimensional image data.

3. The method according to claim 1, wherein at least one of the first medical image data and/or the second digital medical image data comprises radiographic two-dimensional image data.

4. The method according to claim 1, wherein the stimulation electrode comprises at least two directional mutually spaced apart contacts, and the method further comprising using an image appearance of at least part of each of at least two spaces in between the at least two directional contacts in the set of second digital medical images determine the rotational orientation described by the electrode orientation data.

5. The method according to claim 1, wherein the determining the electrode orientation data comprises determining, by the at least one processor and based on the first medical image data, an image appearance of the asymmetric marker coupled with the stimulation electrode, by at least one of:

segmenting an image appearance of the stimulation electrode in each of a plurality of first digital medical images;

edge detecting of constituents of the plurality of first digital medical images; and/or comparing the image appearance of the stimulation electrode in the set of second digital medical images to previously acquired and predetermined electrode template data describing constructional data of the stimulation electrode.

6. The method according to claim 1, further comprising determining at least one imaging direction at which the set of second digital medical images was generated based on the first medical image data.

7. The method according to claim 6, wherein the determining the at least one imaging direction comprises determining an imaging direction that is perpendicular to the longitudinal axis of the stimulation electrode.

8. The method according to claim 1, further comprising optimizing an imaging parameter of a medical imaging apparatus based on at least one of the first medical image data or the set of second digital medical image data, for generating third medical image data that describes a third medical image of the stimulation electrode.

9. The method according to claim 8, wherein the optimizing the imaging parameter comprises optimizing at least one of an imaging radiation dose, a field of view, a focus, and/or a collimator setting.

10. The method according to claim 8, wherein the generating the third medical image data comprises generating radiography and/or tomography two- or three-dimensional image data.

11. A non-transient computer readable storage medium storing a computer program comprising instructions that, when executed by a processor device of a computer, cause the computer to perform a method of determining a position of a stimulation electrode having asymmetric properties provided to the stimulation electrode by directional contacts of the stimulation electrode and/or by an asymmetric marker coupled with the stimulation electrode, the method comprising:

acquiring first medical image data that describes a first digital medical image of an anatomical body part and the stimulation electrode;

determining electrode position data based on the first medical image data, wherein the electrode position data describes a position of an artifact in the first medical image data representing an imaging response of the stimulation electrode having the asymmetric properties to imaging radiation used to generate the first medical image data, wherein the electrode position data describes a position of the stimulation electrode relative to the anatomical body part;

acquiring second digital medical image data based on the position of the artifact described in the electrode position data, wherein the second digital medical image data describes a set of second digital medical images of the stimulation electrode; and determining electrode orientation data based on the second digital medical image data, wherein the electrode orientation data describes a rotational orientation of the stimulation electrode around a longitudinal axis of the stimulation electrode.

12. A medical system comprising:

at least one computer comprising a processor and a non-transitory storage medium storing a computer program thereon, wherein the processor is configured to determine, by the at least one processor, an image appearance of a rotationally asymmetric orientation marker by comparing an image appearance of a stimulation electrode having asymmetric properties provided to the stimulation electrode by the rotationally asymmetric orientation marker coupled with the stimulation electrode in a set of second digital medical images to previously acquired and predetermined electrode template data describing constructional data of the stimulation electrode;

a non-transitory electronic data storage device storing at least the electrode template data;

a first medical imaging apparatus configured to generate the first medical image data;

a second medical imaging apparatus configured to generate the second digital medical image data based on orientation marker data determined based on a position of an artifact in the first medical image data representing an imaging response of the rotationally asymmetric orientation marker to imaging radiation used to generate the first medical image data, wherein the at least one computer is operably coupled to:

the first medical imaging apparatus for acquiring, from the first medical imaging apparatus, the first medical image data;

the second medical imaging apparatus for acquiring, from the second medical imaging apparatus, the second digital medical image data; and the at least one non-transitory electronic data storage device for acquiring, from the data storage device, at least the electrode template data.

13. The system according to claim 12, wherein the first medical imaging apparatus and the second medical imaging apparatus are identical.

* * * * *